(12) United States Patent
Kim

(10) Patent No.: US 11,433,250 B2
(45) Date of Patent: Sep. 6, 2022

(54) SKIN TREATMENT APPARATUS USING FRACTIONAL PLASMA

(71) Applicant: SEOULIN MEDICARE CO., LTD., Hwaseong-si (KR)

(72) Inventor: Byoung Choul Kim, Seongnam-si (KR)

(73) Assignee: SEOULIN MEDICARE CO., LTD., Hwaseong-si (KR)

( * ) Notice: Subject to any disclaimer, the term of this patent is extended or adjusted under 35 U.S.C. 154(b) by 423 days.

(21) Appl. No.: 16/500,945

(22) PCT Filed: Feb. 1, 2018

(86) PCT No.: PCT/KR2018/001362
§ 371 (c)(1),
(2) Date: Oct. 4, 2019

(87) PCT Pub. No.: WO2018/190500
PCT Pub. Date: Oct. 18, 2018

(65) Prior Publication Data
US 2020/0108262 A1    Apr. 9, 2020

(30) Foreign Application Priority Data
Apr. 12, 2017   (KR) .......................... 10-2017-0047278

(51) Int. Cl.
*A61N 1/44*   (2006.01)
*A61N 1/04*   (2006.01)
*H05H 1/24*   (2006.01)

(52) U.S. Cl.
CPC ............. *A61N 1/44* (2013.01); *A61N 1/0408* (2013.01); *A61N 1/0472* (2013.01); *H05H 1/2406* (2013.01)

(58) Field of Classification Search
None
See application file for complete search history.

(56) References Cited

U.S. PATENT DOCUMENTS 5,683,366 A * 11/1997 Eggers ................... A61B 18/12
604/114
6,244,211 B1 * 6/2001 Nishikawa .......... C23C 16/4401
118/723 AN (Continued)

FOREIGN PATENT DOCUMENTS

KR    10-1422823 B1    8/2014
KR    10-1568380 B1    11/2015
(Continued)

*Primary Examiner* — Carl H Layno
*Assistant Examiner* — Manolis Pahakis
(74) *Attorney, Agent, or Firm* — Rabin & Berdo, P.C.

(57) ABSTRACT

The present invention relates to a skin treatment apparatus using plasma, in which a plasma generator includes an electrode plate an upper dielectric body independent electrode parts and a lower dielectric body. The independent electrode parts are a plurality of pieces of silver paste or flexible printed circuit boards (FPCBs) which are spaced a certain distance apart from each other. According to the present invention, electrode parts operate independently to prevent a plasma concentration phenomenon and uniformly generate plasma. According to the present invention, a plasma generator configured as described above is easy to form in a convex shape, and a convex plasma generator is applicable to a curved region of the skin to be treated, e.g., a palm. Furthermore, the convex plasma generator is capable of more uniformly generating plasma and is particularly effective for treatment of a long and round cylindrical object to be treated, e.g., the vagina of a woman.

5 Claims, 5 Drawing Sheets

(56) References Cited

U.S. PATENT DOCUMENTS

| | | | | |
|---|---|---|---|---|
| 6,413,255 B1* | 7/2002 | Stern | A61B 18/14 | 606/41 |
| 6,509,689 B1* | 1/2003 | Kim | H01J 11/14 | 313/586 |
| 6,632,323 B2* | 10/2003 | Kim | C23C 16/45595 | 156/345.43 |
| 9,339,572 B2 | 5/2016 | Tsai | A61L 2/0088 | |
| 9,386,678 B2* | 7/2016 | Yagi | H01T 23/00 | |
| 9,572,241 B1* | 2/2017 | Eckert | H05H 1/2406 | |
| 10,420,852 B2* | 9/2019 | Pouvesle | H05H 1/46 | |
| 11,123,446 B2* | 9/2021 | Louis | A47L 13/26 | |
| 2002/0122896 A1* | 9/2002 | Kim | H01J 37/32082 | 427/569 |
| 2002/0129902 A1* | 9/2002 | Babayan | H01J 37/32009 | 156/345.43 |
| 2002/0187066 A1* | 12/2002 | Yu | A61L 2/0011 | 422/23 |
| 2003/0052096 A1* | 3/2003 | Crowe | H05H 1/2406 | 219/121.43 |
| 2003/0070760 A1* | 4/2003 | Kim | H01J 37/32009 | 156/345.43 |
| 2003/0129107 A1* | 7/2003 | Denes | H01J 37/32532 | 422/186.21 |
| 2005/0143726 A1* | 6/2005 | Bortkiewicz | A61B 18/148 | 606/49 |
| 2007/0037408 A1* | 2/2007 | Tachibana | C23C 16/515 | 438/778 |
| 2008/0045879 A1* | 2/2008 | Prausnitz | A61K 41/0047 | 604/20 |
| 2009/0160341 A1* | 6/2009 | Justel | C09K 11/7774 | 313/637 |
| 2010/0016936 A1* | 1/2010 | Stevenson | A61B 18/1492 | 607/116 |
| 2010/0036369 A1* | 2/2010 | Hancock | A61B 18/1815 | 606/33 |
| 2010/0145253 A1* | 6/2010 | Gutsol | A61N 1/40 | 604/20 |
| 2011/0018444 A1* | 1/2011 | Pouvesle | H05H 1/2406 | 315/111.21 |
| 2011/0141649 A1* | 6/2011 | Villemejane | A61N 1/0472 | 216/33 |
| 2012/0259270 A1* | 10/2012 | Wandke | A61N 1/0476 | 604/23 |
| 2013/0345620 A1* | 12/2013 | Zemel | A61B 18/042 | 604/24 |
| 2014/0217882 A1* | 8/2014 | Yagi | B01J 19/088 | 313/268 |
| 2015/0209595 A1* | 7/2015 | Kalghatgi | A61N 1/44 | 604/20 |
| 2015/0343231 A1* | 12/2015 | Sanders | A61L 2/14 | 607/2 |
| 2017/0135678 A1* | 5/2017 | Kalghatgi | A61B 5/14514 | |
| 2017/0136252 A1* | 5/2017 | Weltmann | A61L 2/14 | |
| 2017/0231680 A1* | 8/2017 | Mahrenholz | A61N 1/44 | 606/34 |
| 2017/0326347 A1* | 11/2017 | Kalghatgi | A61B 18/042 | |
| 2018/0103991 A1* | 4/2018 | Linhart | A61B 18/1477 | |
| 2018/0126183 A1* | 5/2018 | Nijdam | H05H 1/2406 | |
| 2018/0133496 A1* | 5/2018 | Zuidervaart | A61N 1/44 | |
| 2018/0206321 A1* | 7/2018 | Morfill | H01J 37/32532 | |
| 2019/0070407 A1* | 3/2019 | Kim | A61B 18/042 | |
| 2019/0104605 A1* | 4/2019 | Van Abeelen | A61L 2/0011 | |
| 2019/0105506 A1* | 4/2019 | Bourquin | A61N 1/44 | |
| 2019/0184187 A1* | 6/2019 | Lee | A61N 1/08 | |
| 2019/0223280 A1* | 7/2019 | Wandke | A61N 1/44 | |
| 2020/0038530 A1* | 2/2020 | Yildirim | A61H 23/0263 | |
| 2020/0038673 A1* | 2/2020 | Yildirim | A61L 2/14 | |
| 2020/0221564 A1* | 7/2020 | Wandke | H05H 1/2406 | |
| 2021/0112651 A1* | 4/2021 | Lee | A61L 9/22 | |
| 2021/0260394 A1* | 8/2021 | Wunderl | H05H 1/2406 | |

FOREIGN PATENT DOCUMENTS

| | | |
|---|---|---|
| KR | 10-2016-0111119 A | 9/2016 |
| KR | 2016-0134593 A | 11/2016 |

* cited by examiner

SKIN TREATMENT APPARATUS USING FRACTIONAL PLASMA

CROSS REFERENCE TO RELATED APPLICATIONS

This application is a National Phase filing under 35 U.S.C. § 371 of PCT/KR2018/001362 filed on Feb. 1, 2018; which application in turn claims priority to Application No. 10-2017-0047278 filed in Korea on Apr. 12, 2017. The entire contents of each application are hereby incorporated by reference.

TECHNICAL FIELD

The present invention relates to a skin treatment apparatus using plasma, and more particularly, to a skin treatment apparatus using fractional plasma, in which a dielectric body is provided to generate soft plasma by inducing a dielectric barrier discharge to occur between the skin and a plasma generator, and a plurality of independent electrodes are configured using silver paste to prevent a plasma concentration phenomenon.

BACKGROUND OF THE INVENTION

A state of a material may be divided into a solid state, a liquid state, and a gaseous state. When energy is applied to a gaseous material, electrons are separated from atoms or molecules to cause a plasma state in which electrons, ions, and neutral particles (molecules and atoms) are mixed.

In the plasma state, the electrons can be easily accelerated in various ways, the neutral particles may collide with molecules of a material to be processed to produce chemically active species, and the ions form conditions causing chemical reactions to occur at a surface of the material to be processed so that the active species may cause an active chemical action on the surface of the material.

That is, the plasma contains, for example, chemically active species, such as oxy-, hydroxyl-, and nitrogen radicals, electronically excited atoms or molecules, and ultraviolet (UV) photons, ions, and radicals, which lightly and gently tap an affected area to stimulate and sterilize the affected area, as if the affected area is showered, while moving along an electric field.

Plasma is easier to generate in a low-pressure vacuum state of about 1 mTorr to 100 Torr than at atmospheric pressure. However, in order to generate plasma at such low pressures, there are various constraints, e.g., it is necessary to manufacture a vacuum container and attach a vacuum pump thereto to maintain a vacuum. For this reason, much research has been conducted on a method of generating plasma under atmospheric pressure other than a vacuum state, and thus, recently, plasma has been generated under pressure equal to or greater than the atmospheric pressure.

With characteristics of plasma and the development of a generation method thereof, plasma has been used in various fields of industry. Many practical attempts have been made to use a plasma technique in medical fields such as sterilization of micro-organisms, hemostasis of wounds, teeth whitening, and killing cancer cells. In particular, a technique for using plasma for skin treatment has been shown to have potential earlier than other fields, and in-depth research has been conducted thereon.

Plasma may be classified into a thermal plasma discharge and a non-thermal plasma discharge according to a method of generating plasma. The thermal plasma discharge is a method of ionizing a gas by heat, and the non-thermal plasma method is a method of ionizing a gas by mainly heating electrons while minimizing heating of the gas. The non-thermal plasma discharge method is also referred to as non-equilibrium plasma method, because only electrons have a high temperature but remaining ions and neutral particles are maintained at low temperatures, thereby causing thermal unbalance.

Non-thermal plasma is generated by the following process. When two planar conductors are separated from each other by a distance d and a voltage V is applied thereto, an electric field E is generated under a condition of E=V/d. In this case, when the voltage V reaches a certain level or higher, charged particles (electrons) are accelerated by the electric field E, are provided with energy and thus collide with neutral gas atoms or molecules. Thus, atoms and molecules are ionized to a plasma state in which electrons, ions, and neutral particles (molecules and atoms) are mixed.

In the plasma generator of the related art (KR10-1568380 B1), as illustrated in FIG. 1, a plasma generator is provided in the form of a tip at the end of a cylindrical housing 10 of a handpiece type and includes an electrode 20 to which a frequency is applied from a transformer, a disc-shaped substrate 30 located on a lower surface of the electrode 20 and having a plurality of through-holes 31 vertically formed at uniform intervals to be in contact with the electrode 20, and a dielectric body 40 in contact with a lower surface of the substrate 30.

The through-holes 31 are formed in the substrate 30, similar to the shape of holes of a shower, and the inner surface thereof may be coated or plated with a conductive material. The dielectric body 40 may be formed of a material such as quartz, sapphire, glass, ceramic, or polymer film, and have a thickness in a range of about 0.1 mm to 3 mm and a relative dielectric constant in a range of about 4 to 18.

Therefore, power is delivered from the electrode 20 to the dielectric body 40 via through the through-holes 13 of the substrate 30 in a manner similar to a shower manner, and thus, an R-L-C series circuit is formed between the dielectric body 40 and skin S so that the skin S may be in the form of circuit having a low impedance and thus a weak current that does not harm the human body may flow through the skin S. In this case, plasma P is generated between the skin S and the dielectric body 40 which are in contact with each other by a gentle dielectric barrier discharge based on a plasma shower method.

However, according to the related art, a high frequency and high voltage are applied to the electrode 20 and power is transferred from the electrode 20 to the dielectric body 40 via the through-holes 13 of the substrate 30 in a manner similar to a shower manner, thereby generating plasma between the dielectric body 40 and the skin S. Because all the through-holes 13 are connected to one electrode 20, the through-holes 13 cannot operate as independent electrodes and thus the plasma may be unevenly generated in the through-holes 13, i.e., a plasma concentration phenomenon may occur.

In addition, the plasma generator of the related art is applicable to a generally flat region, such as face or the back of a hand, but is not applicable to a curved object to be treated, such as a palm, and particularly, a long and round cylindrical object to be treated, such as the vagina of a woman.

Summary of the Invention

Technical Problem

To address the above-mentioned problems, the present invention is directed to providing a skin treatment apparatus in which independent electrode parts each formed of silver paste or a flexible printed circuit board (FPCB) are formed between an upper dielectric body and a lower dielectric body to be spaced a certain distance apart from each other.

The present invention is also directed to providing a skin treatment apparatus for skin treatment in which a plasma generator is formed in a convex shape, such as a cylindrical shape, a cylindrical fragment shape, a spherical shape, or a partially spherical shape.

Technical Solution

One aspect of the present invention provides a skin treatment apparatus for skin treatment using plasma generated by a plasma generator, wherein the plasma generator includes an electrode plate connected to the high-voltage module; an upper dielectric body below the electrode plate; a plurality of independent electrode parts located below the upper dielectric body and spaced a certain distance from each other; and a lower dielectric body below the plurality of independent electrode parts, and power from the electrode plate is supplied to the upper electric body, the plurality of independent electrode parts, and the lower dielectric body to generate plasma in a space between the lower dielectric body and the skin.

In the skin treatment apparatus for skin treatment using fractional plasma according to the present invention, the plasma generator may be convex toward the skin.

In the skin treatment apparatus for skin treatment using fractional plasma according to the present invention, the plasma generator may be formed in a shape among a cylindrical shape, a cylindrical fragment shape, a spherical shape, and a partially spherical shape.

In the skin treatment apparatus for skin treatment using fractional plasma according to the present invention, the plurality of independent electrode parts may include silver paste or flexible printed circuit boards (FPCBs).

[Advantageous Effects]

According to the present invention, independent electrode parts each formed of silver paste or a flexible printed circuit board (FPCB) are formed between an upper dielectric body and a lower dielectric body to be spaced a certain distance apart from each other, thereby preventing a plasma concentration phenomenon from occurring.

According to the present invention, a plasma generator is formed in a convex shape for effective treatment of a curved object to be treated, such as a palm. In particular, when the plasma generator is formed in a cylindrical shape or one end of the cylindrical body, it is possible to effectively treat a long and round cylindrical object to be treated, such as the vagina of a woman.

DETAILED DESCRIPTION OF THE INVENTION

Hereinafter, exemplary embodiments of the present invention will be described in more detail with reference to the accompanying drawings.

Figure 1:
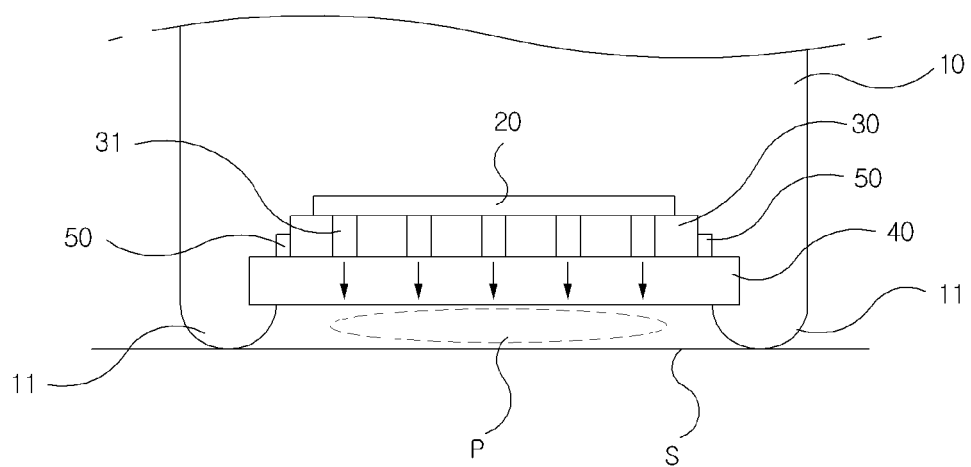
FIG. 1 illustrates a skin treatment apparatus using plasma according to the related art.
Figure 2:
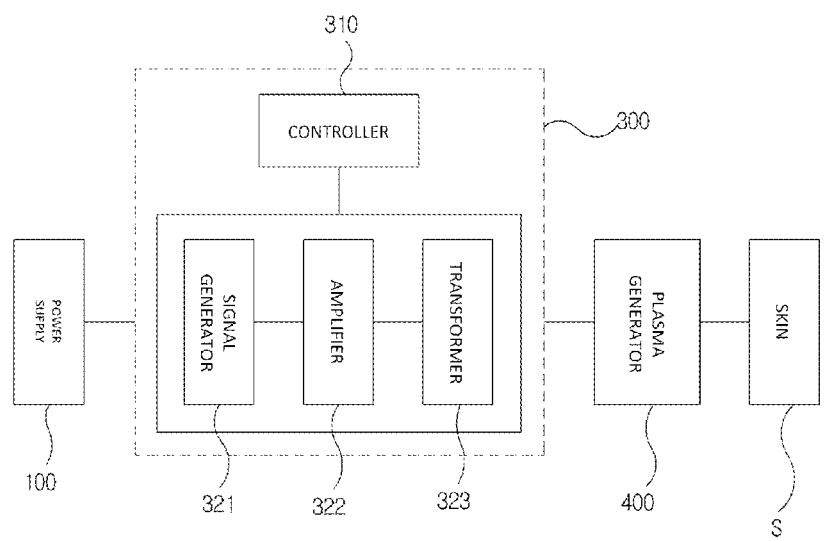
FIG. 2 is a block diagram illustrating an overall structure of the present invention.

As illustrated in FIG. 2, a skin treatment apparatus using plasma according to the present invention includes a power supply 100, a high-voltage module 300, and a plasma generator 400. The high-voltage module 300 includes a controller 310, a signal generator 321, an amplifier 322, and a transformer 323.

The power supply 100 may be an external power source or may be a small-sized portable battery.

The controller 310 of the high-voltage module 300 controls direct-current (DC) power output from the power supply 100 to be converted into high-frequency and high-voltage alternating-current (AC) power. The signal generator 321 of the high-voltage module 300 generally generates a frequency of 20 kHz or more. The amplifier 322 of the high-voltage module 300 is matched with impedance in a range of 5 to 50 W.

The transformer 323 of the high-voltage module 300 supplies the frequency output from the amplifier 322 of the high-voltage module 300 to the plasma generator 400 to generate plasma.

Figure 3:
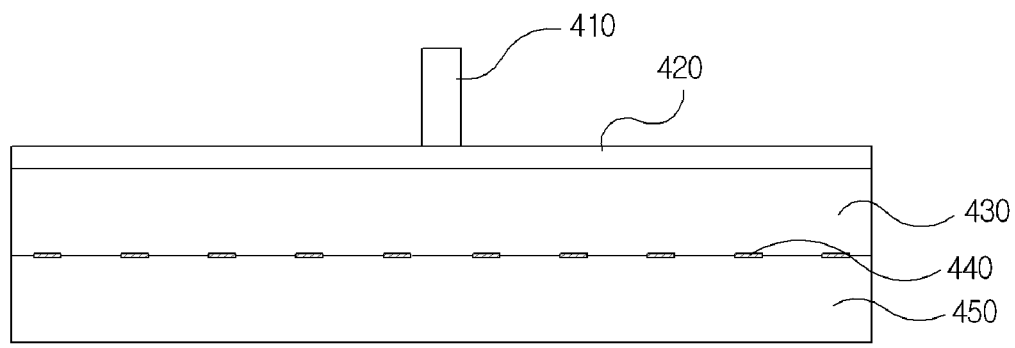
FIG. 3 is a diagram illustrating main components of a plasma generator according to the present invention.

FIG. 3 illustrates main components of the plasma generator 400 which generates plasma using high-voltage and high-frequency power output from the high-voltage module 300.

The plasma generator 400 includes a power connection part 410 for transmitting power from the transformer 323 of the high-voltage module 300, an electrode plate 420 to which high-voltage and high-frequency power is supplied via the power connection part 410, and an upper dielectric body 430 and a lower dielectric body 450 below the electrode plate 420. A plurality of independent electrode parts 440 are printed between the upper dielectric body 430 and the lower dielectric body 450 to be spaced a certain distance from each other.

The skin treatment apparatus using plasma according to the present invention configured as described above operates as described below.

First, when a skin treatment device of the present invention is placed on a region of the skin to be treated and a start button is pressed, the power supply 100 supplies DC power to the high-voltage module 300, and the high-voltage module 300 converts the DC power into high-voltage and high-frequency AC power via the controller 310, the signal generator 321, the amplifier 322, and the transformer 323 and supplies the AC power to the electrode plate 420 via the power connection part 410 of the plasma generator 400.

The power supplied to the electrode plate 420 passes through the upper dielectric body 430 and the independent electrode parts 440 printed between the upper dielectric body 430 and the lower dielectric body 450.

Figure 4:
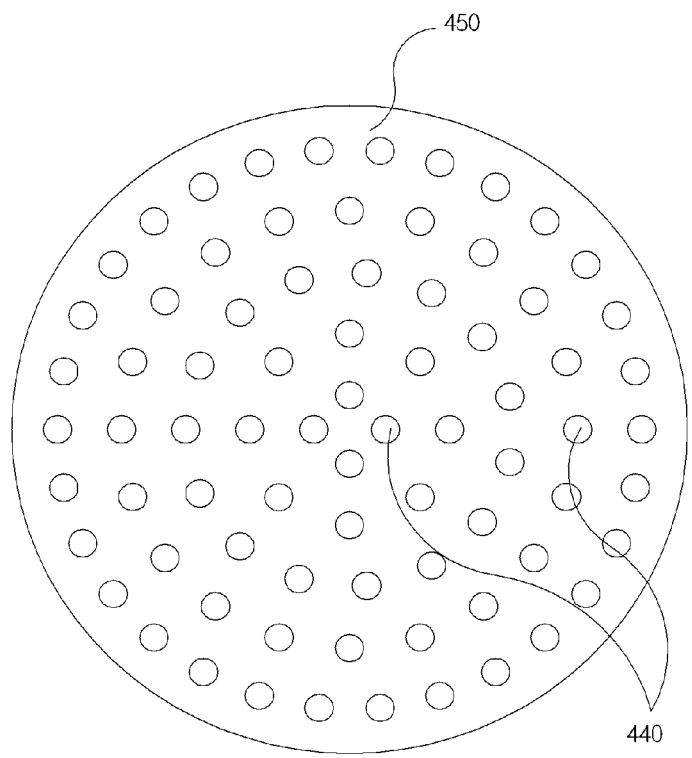
FIG. 4 is a diagram illustrating independent electrode parts of a plasma generator according to the present invention.

The independent electrode parts 440 may be a plurality of pieces of silver paste or FPCBs which are spaced a certain distance from each other as illustrated in FIG. 4.

Figure 5:
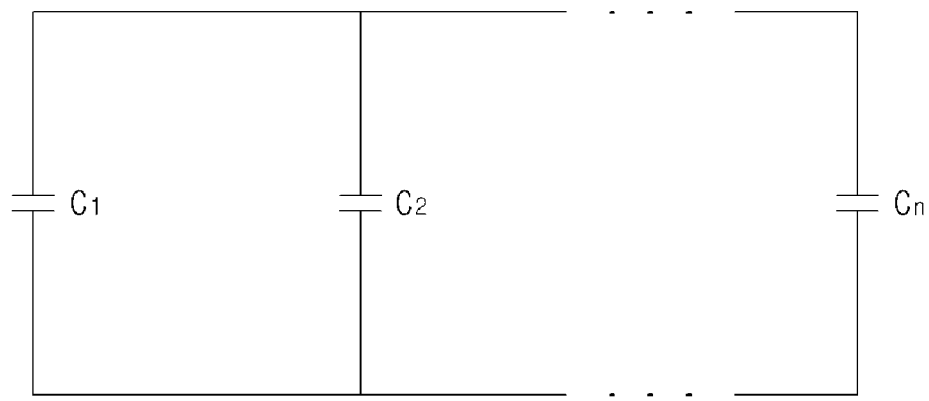
FIG. 5 is an equivalent circuit of the independent electrode parts of FIG. 4.

An equivalent circuit of the independent electrode parts 440 is as illustrated in FIG. 5. That is, the independent electrode parts 440 may act as cell capacitors and thus may be represented by C1, C2, ... Cn. The values of the cell capacitors C1, C2, ... Cn may be adjusted by adjusting the cross-sectional areas of the independent electrode parts 440. That is, because a capacitance is proportional to a cross-sectional area, a capacitance of a cell capacitor may be increased by increasing a cross-sectional area of an independent electrode part or reduced by reducing the cross-sectional area of the independent electrode part or all cell capacitors may be adjusted to have the same capacitance.

As described above, according to the present invention, a plurality of electrode parts formed of silver paste or FPCBs are not directly connected to the electrode plate 420 and operate independently, and thus, a phenomenon in which plasma is concentrated on a side that occurs in the related art may be prevented and plasma may be uniformly generated at the independent electrode parts.

In addition, the present invention employs thin independent electrode parts such as silver paste or FPCBs and thus a convex plasma generator described below may be easily configured.

There is a curved object to be treated, such as a palm. Such an object is inconvenient to treat using a flat plasma generator. In this case, when the plasma generator 400 according to the present invention is formed in a convex shape, a curved object to be treated, such as a palm, may be effectively treated therewith.

In addition, a more uniform amount of plasma may be generated by a convex plasma generator as described with reference to FIG. 6 below.

Figure 6:
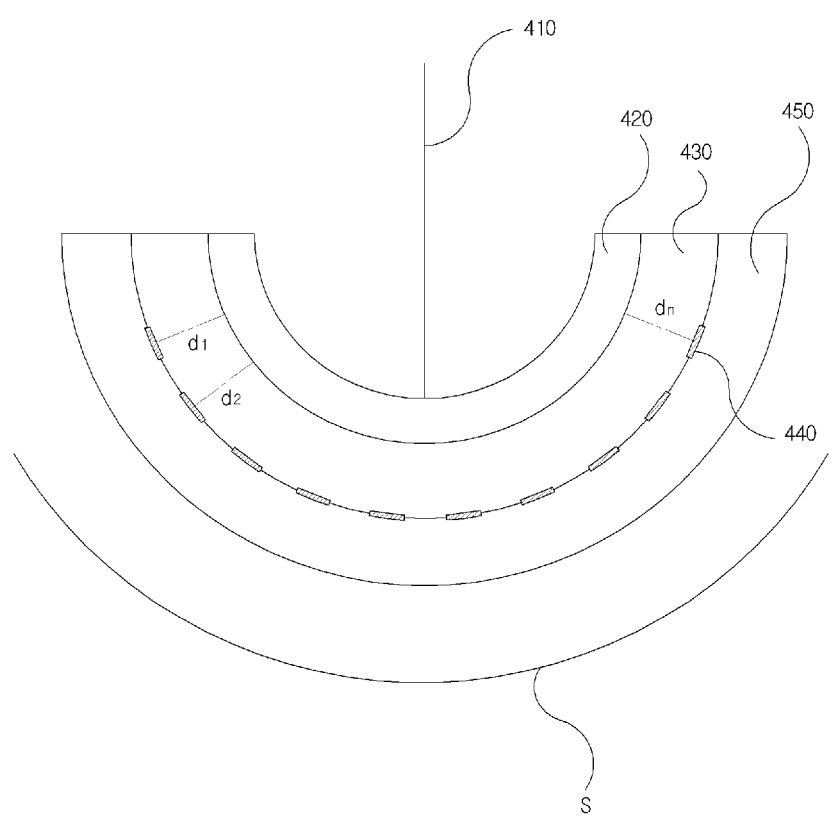
FIG. 6 is a diagram illustrating a convex plasma generator according to the present invention.

Because all components of the plasma generator of FIG. 6, i.e., an electrode plate, an upper dielectric body, and a lower dielectric body are in a convex shape, the distances d1, d2, ... , dn between the electrode plate 420 and the independent electrode parts 440 are the same. Because a capacitance is affected by the distance between two electrodes and the distances d1, d2, ... , dn are the same, capacitances between the electrode plate 420 and the independent electrode parts 440 are the same and thus plasma may be evenly emitted to the skin.

When a plasma generator is formed in a convex shape, e.g., a cylindrical fragment or a cylindrical shape, the skin of a long and round cylindrical shape, such as the vagina of a woman, may be effectively treated.

Figure 7:
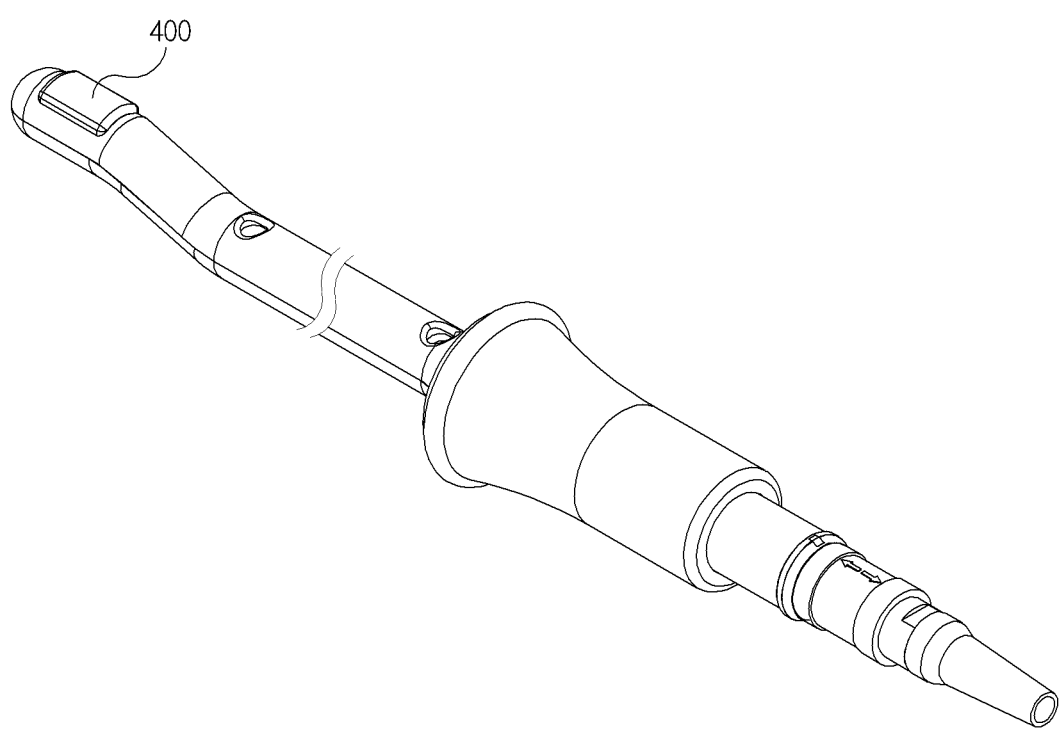
FIG. 7 is a diagram illustrating an example in which a plasma generator having a cylindrical convex fragment shape according to the present invention is attached to an outer circumferential surface of a skin treatment apparatus.

As illustrated in FIG. 7, the plasma generator 400 may be formed in a convex shape (a cylindrical fragment) and attached in an arch along an outer circumferential surface of an end of a skin treatment apparatus within a range of 30° to 180°. Preferably, the arch is 90 degrees.

In this case, the plasma generator 400 may have a size of about 8 mm in width and 20 mm in length.

Figure 8:
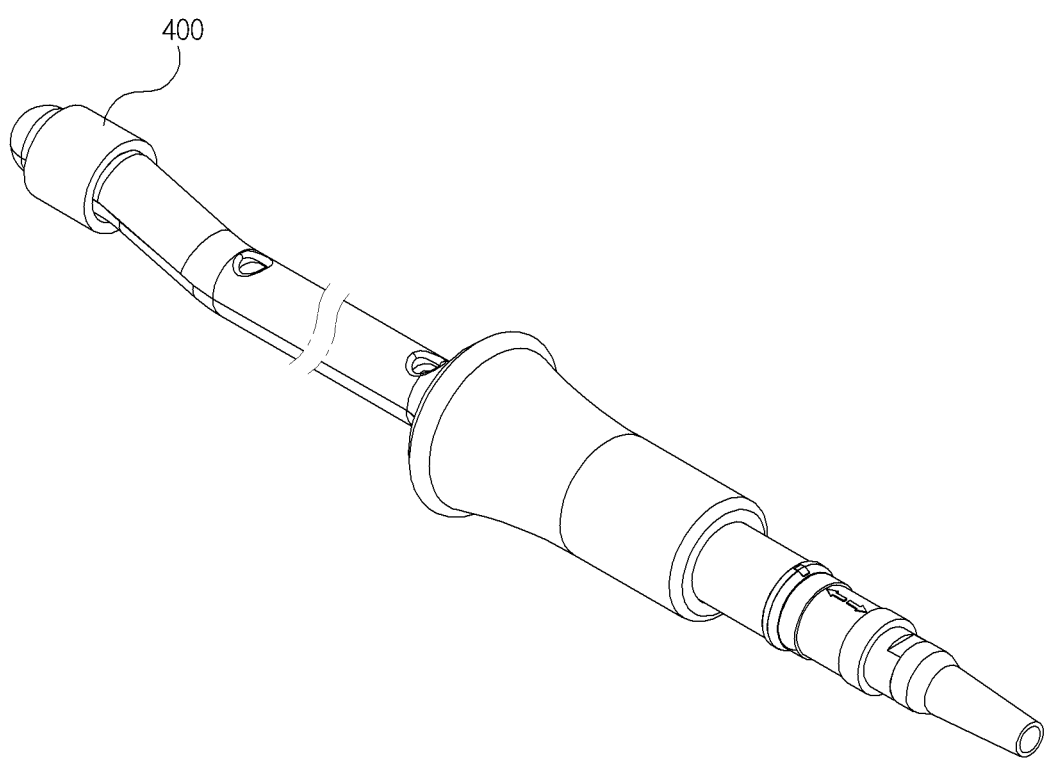
FIG. 8 is a diagram illustrating an example in which a plasma generator having a cylindrical convex fragment shape according to the present invention is attached to an entire outer circumferential surface of a skin treatment apparatus.

Alternatively, as illustrated in FIG. 8, the plasma generator 400 may be formed in a convex (cylindrical) shape and attached to the entire outer circumferential surface of an end of the skin treatment apparatus. Similarly, the plasma generator 400 may be about 20 mm long.

As described above, when a plurality of pieces of silver paste are printed between two dielectric bodies to be spaced a certain distance apart from each other and the dielectric bodies are formed in a convex shape, a long and round cylindrical object to be treated may be more effectively treated.

A skin treatment apparatus using plasma according to the present invention described above is not limited to the above embodiments, and various modifications may be made therein by those of ordinary skill in the art without departing from the technical scope claimed in the following claims.

The invention claimed is:

1. A skin treatment apparatus using fractional plasma, comprising:
a high-voltage module including a transformer; and
a plasma generator,
wherein the skin treatment apparatus conducts skin treatment using plasma generated by the plasma generator,
the plasma generator comprises:
an electrode plate connected to the high-voltage module;
an upper dielectric body below the electrode plate;
a plurality of independent electrode parts located below the upper dielectric body and spaced a certain distance from each other, the plurality of electrode parts acting as cell capacitors and being unconnected to an external power source; and
a lower dielectric body below the plurality of independent electrode parts, the lower dielectric body impeding flow of current between the plurality of independent electrode parts and skin, and
wherein power which is supplied to the electrode plate by the high-voltage module is supplied to the upper dielectric body, the plurality of independent electrode parts, and the lower dielectric body to generate plasma in a space between the lower dielectric body and the skin.

2. The skin treatment apparatus of claim 1, wherein the plasma generator is convex toward the skin.

3. The skin treatment apparatus of claim 2, wherein the plasma generator is formed in a shape among a cylindrical shape, a cylindrical fragment shape, a spherical shape, and a partially spherical shape.

4. The skin treatment apparatus of claim 1, wherein the plurality of independent electrode parts comprise silver paste or flexible printed circuit boards.

5. The skin treatment apparatus of claim 1, wherein the high-voltage module further includes a controller, a signal generator and an amplifier.

* * * * *